(12) United States Patent
Kim et al.

(10) Patent No.: US 8,727,558 B2
(45) Date of Patent: May 20, 2014

(54) MEDICAL HEADLAMP FOR TRACKING EYE LOCATIONS

(75) Inventors: SungMin Kim, Gyeonggi-do (KR); Hyo Joon Kim, Jeollabuk-do (KR); Wonha Kim, Gyeonggi-do (KR); Sang Hoon Hong, Gyeonggi-do (KR)

(73) Assignee: Dongguk University Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 13/515,766

(22) PCT Filed: Feb. 6, 2012

(86) PCT No.: PCT/KR2012/000852
§ 371 (c)(1),
(2), (4) Date: Jun. 12, 2013

(87) PCT Pub. No.: WO2012/118282
PCT Pub. Date: Sep. 7, 2012

(65) Prior Publication Data
US 2013/0322053 A1 Dec. 5, 2013

(30) Foreign Application Priority Data
Feb. 28, 2011 (KR) .......................... 10-2011-0017542

(51) Int. Cl.
*F21V 21/084* (2006.01)
(52) U.S. Cl.
USPC ............................ 362/105; 362/106; 362/286

(58) Field of Classification Search
USPC ............. 362/8, 105, 106, 276, 285, 286, 287, 362/386, 418, 427, 804
See application file for complete search history.

(56) References Cited

U.S. PATENT DOCUMENTS

2001/0021108 A1* 9/2001 Shimada et al. ............... 362/804
2012/0294478 A1* 11/2012 Publicover et al. ........... 362/105

FOREIGN PATENT DOCUMENTS

| JP | 2002-324403 | 11/2002 |
| JP | 2003-036704 | 2/2003 |
| KR | 2006-0131775 | 12/2006 |
| KR | 2008-0086143 | 9/2008 |

* cited by examiner

*Primary Examiner* — Y My Quach Lee
(74) *Attorney, Agent, or Firm* — Swanson & Bratschun, LLC

(57) ABSTRACT

Provided is a medical headlamp including a main body put on a head, a driving unit installed and connected to one side of the main body and to provide a driving force, a location adjustment unit installed and connected to one side of the driving unit, a lamp unit installed and connected to one side of the location adjustment unit to move along with a movement of the location adjustment unit, and irradiate light onto one side of a front end thereof, a capturing unit installed and connected to one side of the main body and to capture eye locations, a control unit installed and connected to the driving unit and the capturing unit to analyze an image captured by the capturing unit, calculate the eye locations, and operate the driving unit according to the calculated eye calculation, and a power supply unit installed and connected to the control unit, the driving unit, and the lamp unit and to apply a current thereto.

4 Claims, 2 Drawing Sheets

MEDICAL HEADLAMP FOR TRACKING EYE LOCATIONS

CROSS-REFERENCE TO RELATED APPLICATION

This application is a 35 U.S.C. §371 national phase application of PCT/KR2012/000852, filed on Feb. 6, 2012, entitled "Medical headlamp for tracking eye locations", which application claims priority to and the benefit of Korean Patent Application No. 2011-0017542, filed Feb. 28, 2011, the disclosure of which is incorporated herein by reference in its entirety.

BACKGROUND

1. Field of the invention

The present invention relates to a medical headlamp, and more particularly to, a medical headlamp for tracking eye locations when a surgeon diagnoses or treats a patient, a direction of a lamp in which light is irradiated is adjusted according to the eye locations of the surgeon without a direct and manual operation of the headlamp so that light can be irradiated onto a dark affected part or a desired part.

2. Discussion of Related Art

In general, headlamps are used by attaching to head bands, hats, or helmets in fields such as mining industrial fields, medical fields, in particular, surgical operations.

Such headlamps can advantageously illuminate a range actually seen by persons wearing the headlamps without fixed floodlights or portable lamps.

In particular, in a case where the headlamps are used for medical applications, when a surgeon checks an affected part or performs surgery, the surgeon can more easily perform a medical operation by illuminating a desired part.

Nevertheless, since the medical headlamp is attached to a head of a surgeon irrespective to the surgeon's eyes, in a case where a location of the medical headlamp is adjusted during surgery, a nurse other than an operating surgeon manually adjusts the direction of the medical headlamp attached to the surgeon's head in order to prevent a patient from being contaminated.

In this regard, if the surgeon directly adjusts the medical headlamp attached to the surgeon's head, a desired location of the medical headlamp can be more promptly and precisely established, however, the surgical gloves are contaminated since the surgeon directly adjusted the medical headlamp.

DETAILED DESCRIPTION OF THE INVENTION

Technical Problem

The present invention provides a medical headlamp for capturing a surgeon's eyes by using a capturing unit, analyzing information regarding a captured image, and calculating eye locations so that a direction of the medical headlamp in which light is irradiated automatically corresponds to the surgeon's eyes according to the calculated eye locations.

The present invention also provides a headlamp included in a medical headlamp and capable of adjusting a range of light irradiated by a lamp.

Technical Solution

According to an aspect of the present invention, there is a medical headlamp including a main body put on a head, a driving unit installed and connected to one side of the main body and to provide a driving force, a location adjustment unit installed and connected to one side of the driving unit, a lamp unit installed and connected to one side of the location adjustment unit to move along with a movement of the location adjustment unit and irradiating light onto a side of a front end thereof, a capturing unit installed and connected to one side of the main body and for capturing eye locations, a control unit installed and connected to the driving unit and the capturing unit to analyze an image captured by the capturing unit, calculate the eye locations, and operate the driving unit according to the calculated eye calculation, and a power supply unit installed and connected to the control unit, the driving unit, and the lamp unit and to apply a current thereto.

Advantageous Effects

The effect of a medical headlamp according to the present invention is that an angle of the medical headlamp in which light is irradiated is controlled to automatically correspond to a surgeon's eyes, i.e. eye locations.

BEST MODE

The present invention provides a medical headlamp comprising a main body put on a head, a driving unit installed and connected to one side of the main body and to provide a driving force, a location adjustment unit installed and connected to one side of the driving unit, a lamp unit installed and connected to one side of the location adjustment unit to move along with a movement of the location adjustment unit, and irradiate light onto a side of a front end thereof, a capturing unit installed and connected to one side of the main body and to capture eye locations, a control unit installed and connected to the driving unit and the capturing unit to analyze an image captured by the capturing unit, calculate the eye locations, and operate the driving unit according to the calculated eye calculation, and a power supply unit installed and connected to the control unit, the driving unit, and the lamp unit and to apply a current thereto.

MODE OF THE INVENTION

The present invention provides a medical headlamp comprising a main body put on a head, a driving unit installed and connected to one side of the main body and to provide a driving force, a location adjustment unit installed and connected to one side of the driving unit, a lamp unit installed and connected to one side of the location adjustment unit to move along with a movement of the location adjustment unit, and irradiate light onto one side of a front end thereof, a capturing unit installed and connected to one side of the main body and for capturing eye locations, a control unit installed and connected to the driving unit and the capturing unit to analyze an image captured by the capturing unit, calculate the eye to locations, and operate the driving unit according to the calculated eye calculation, and a power supply unit installed and connected to the control unit, the driving unit, and the lamp unit and to apply a current thereto.

A headlamp according to the present invention, preferably a medical headlamp, may allow light to be automatically irradiated onto a dark affected part or a desired part according to eye locations of a surgeon, preferably, locations of pupils, without directly manipulating the headlamp in a case where the surgeon is diagnosing or treating a patient, and may include any headlamps as long as they have the above objective.

In particular, the headlamp according to the present invention may be applied to a field, for example, a repair business, mining industry, etc. requiring a headlamp that is put on a user and irradiates light onto a desired location according to the user's eyes, as well as the medical field.

Reference will now be made in detail to the example embodiments, examples of which are illustrated in the accompanying drawing. However, the example embodiments are not limited to the embodiments illustrated hereinafter, and the embodiments herein are rather introduced to provide easy and complete understanding of the scope and spirit of the present invention.

Figure 1:
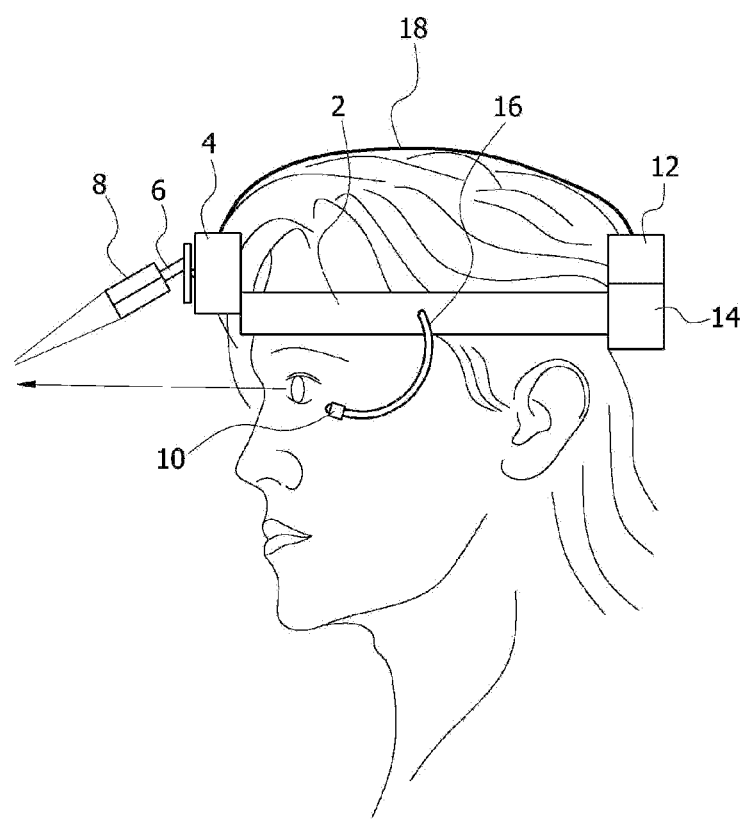
FIG. 1 is a diagram of a construction of a medical headlamp according to an embodiment of the present invention.
Figure 2:
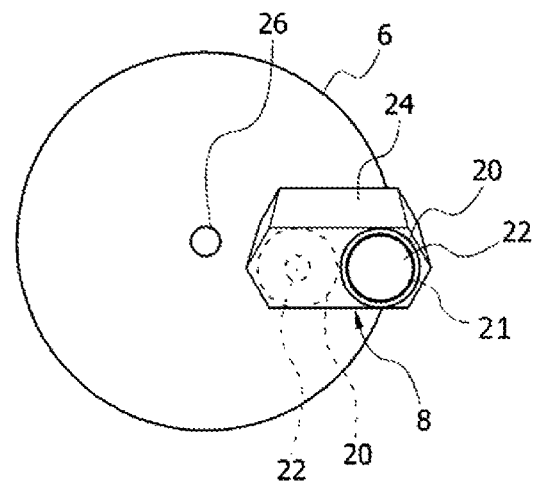
FIG. 2 is a diagram of constructions of a lamp unit and a location adjusting unit of a medical headlamp according to an embodiment of the present invention.
Figure 3:
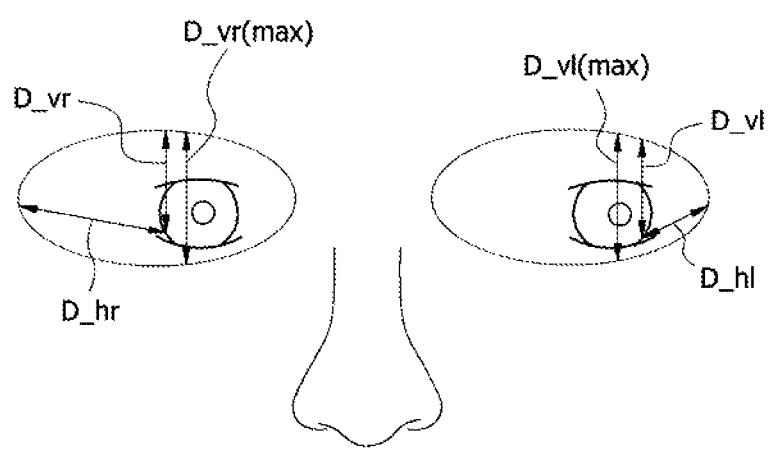
FIG. 3 is a diagram to explain a method of tracking eye locations of a medical headlamp according to an embodiment of the present invention.

FIG. 1 is a diagram of a construction of a medical headlamp according to an embodiment of the present invention. FIG. 2 is a diagram of constructions of a lamp unit and a location adjusting unit of a medical headlamp according to an embodiment of the present invention. FIG. 3 is a diagram to explain a method of tracking eye locations, preferably, the location of pupils, of a medical headlamp according to an embodiment of the present invention.

Referring to FIGS. 1 through 3, the medical headlamp according to the present invention includes a main body 2 put on a head, a driving unit 4 installed and connected to one side of the main body 2 and to provide a driving force, a location adjustment unit 6 installed and connected to one side of the driving unit 4, a lamp unit 8 installed and connected to one side of the location adjustment unit 6 to move along with a movement of the location adjustment unit 6, and irradiate light onto one side of a front end thereof, a capturing unit 10 installed and connected to one side of the main body 2 and to capture eye locations, a control unit 12 installed and connected to the driving unit 4 and the capturing unit 10 to analyze an image captured by the capturing unit 10, calculate the eye locations, and operate the driving unit 4 according to the calculated eye calculation, and a power supply unit 14 installed and connected to the control unit 12, the driving unit 14, and the lamp unit 8 and to apply a current thereto.

The main body 2 according to the present invention is put on a human's head and is not particularly limited to its use as long as it is a general device having the above objective in the field to which the invention pertains.

The main body 2 may preferably use a head band, etc.

The driving unit 4 according to the present invention is installed and connected to one side of the main body 2, specifically, one side of the main body 2 at a human's eyes and provides a driving force to operate the location adjustment unit 6 to which the lamp unit 8 that irradiates light is connected.

In this regard, although the driving unit 4 may use any general devices that provide the driving force, a motor may be preferably used as the driving unit 4.

The location adjustment unit 6 according to the present invention is installed and connected to one side of the driving unit 4, moves according to an operation of the driving unit 4, and adjusts a location of the lamp unit 8.

Further, the location adjustment unit 6 is installed and connected to one side of the lamp unit 8 so that the location of the lamp unit 8 can be adjusted according to the operation of the driving unit 4.

Meanwhile, although the medical headlamp needed additionally to include a driving unit to operate the lamp unit 8 to an x coordinate and another driving unit to operate the lamp unit 8 to a y coordinate in order to automatically adjust the location of the lamp unit 8, the location adjustment unit 6 according to the present invention may adjust the location of the lamp unit 8 by using the single driving unit 4.

To this end, a driving shaft of the driving unit 4, for example, a rotational shaft of the motor, is located in the center 26 of the location adjustment unit 6, and the lamp unit 8 is installed and connected to one side of the location adjustment unit 6 to which the driving shaft is connected and spaced from the center 26 of the location adjustment unit 6 by a predetermined distance, and thus the location adjustment unit 6 according to the present invention rotates by the driving of the driving unit 4 and adjusts the location of the lamp unit 8.

In this regard, although the location adjustment unit 6 is not particularly limited to its shape as long as it may be connected to the driving shaft of the driving unit 4, the location adjustment unit 6 may be preferably in a plate shape, and more preferably in a radially extending plate shape, a disk shape, a plate shape extending in a horizontal direction.

The lamp unit 8 according to the present invention is installed and connected to the location adjustment unit 6 and irradiates light onto the side of the front end thereof to provide the user with illumination. The lamp unit 8 is not particularly limited as long as it is a general lamp unit having the above objective in the field to which the invention pertains.

In this regard, the lamp unit 8 is installed and connected to the location adjustment unit 6 and moves together with a movement of the location adjustment unit 6 that moves according to the driving unit 4 so that the location of the lamp unit 8 changes.

As a specific embodiment, the lamp unit 8 according to the present invention includes a housing 24 to provide an exterior appearance of the lamp unit 8, a main body 20 having a groove 21 and located inside the housing 24, and a lamp 22 inserted into the groove of the main body 20 and placed therein.

In this regard, the lamp 22 moves back and forth inside the main body 20 as the main body 20 rotates, and is configured to change an exposed area of the lamp 22 so that a range of light irradiated by the lamp 22 can change.

As an example, as illustrated in FIG. 2, if the main body 20 of the lamp unit 8 rotates in one direction, the main body 20 moves in a direction of the center 26 of the location adjustment unit 6 connected to the driving shaft of the driving unit 4 and reduces an area onto which light is irradiated, i.e. a size of a spot, so that the irradiation of light can be further concentrated in order to facilitate surgery on a deep and narrow part. If the main body 20 rotates in a direction opposite to the direction, the main body 20 is farther apart from the center 26 and increases the size of the spot so that the range of the irradiated light can be extended.

The capturing unit 10 according to the present invention is installed and connected to one side of the main body 2 and captures eye locations, and is not particularly limited as long as it is a general capturing unit having the above objective in the field to which the invention pertains.

In this regard, the capturing unit 10 may use a camera, for example, a digital camera or a CCD camera, and may be installed and connected to one side edge of a guide bar 16 extending in a horizontal direction from one side surface of the main body 2 in order to prevent a view of a user's from being hidden.

Further, the medical headlamp may include two capturing units 10 when necessary so that the two capturing units 10 can be adjacent to the left and right eyes, and thus the user's left and right eyes can be captured.

The control unit 12 according to the present invention is installed and connected to the driving unit 4 and the capturing unit 10, analyzes an image captured by the capturing unit 10, calculates eye locations, operates the driving unit 4 according to the calculated eye locations, and adjusts a direction of the lamp unit 8 installed and connected to the location adjustment unit 6 so that the lamp unit 8 can correspond to the eye locations and irradiate light.

Although the control unit 12 may use any general control units having the above objective in the field to which the invention pertains, a printed circuit board may be preferably used as the control unit 12.

Further, although a method of calculating the eye locations from the image captured by the capturing unit 10 that is performed by the control unit 12 is not particularly limited, the control unit 12 may use a method of calculating the eye locations by measuring distances between boundaries of pupils and eye regions.

In this regard, the method of calculating the eye locations by measuring distances between boundaries of pupils and eye regions will now be described below.

As illustrated in FIG. 3, D_vr(max) and D_vl(max) denote maximum values of currently open eyes, D_vr and D_vl denote distances between center points of boundaries of a right eye and a left eye and highest points of the open left and right eyes, respectively, and D_hr and D_hl denote distances between the center points of boundaries of the right eye and the left eye and a left corner of the left eye and a right corner of the right eye, respectively. A direction seen by the eyes, i.e. the user's eyes, is calculated by measuring the above parameters.

In connection with the calculation of such user's eyes, in a case where the medical headlamp includes the twp capturing units 10 so that the left and right eyes can be adjacent to the two capturing units 10, after a physical condition in which the distances between the two capturing units 10 and the eyes are the same and a software condition of an image normalization are satisfied, an x coordinate is calculated as x=(D_hr−D_hl), and a y coordinate is calculated as y=(D_vr(max)/2−D_vr) if D_vr(max)≥D_vl(max), if on the other hand D_vr(max)<D_vl(max), y coordinate is calculated as y=(D_vl(max)/2−D_vl). In this regard, a rotation level of the location adjustment unit 6 is calculated according to Equation 1 below by using the calculated x and y coordinates.

$$\text{Rotation Level} = \arctan(y/x) \quad \text{[Equation 1]}$$

The power supply unit 14 according to the present invention is installed and connected to the control unit 12, the driving unit 14, and the lamp unit 8, applies a current thereto, and is not particularly limited as long as it is a general power supply unit having the above objective in the field to which the invention pertains.

In this regard, the power supply unit 14 may be installed and connected to the control unit 12, the driving unit 14, and/or the lamp unit 8 by an electric wire 18. As a specific embodiment, although the power supply unit 14 may be independently located outside the medical headlamp and supply the current to the medical headlamp through the electric wire 18, a rechargeable battery or a battery connected to one side of the main body 2 may be included in the medical headlamp so that the user can move freely.

In this regard, in a case where the power supply unit 14 is installed and connected to one side of the main body 2 of the medical headlamp, the power supply unit 14 may be included in another side of the main body 2 facing one side thereof in which the lamp unit 8 is located.

Further, the power supply unit 14 may be integrally formed with the control unit 12.

An operation of the medical headlamp according to the present invention having the above-described construction will now be described below.

First, a user who puts on the medical headlamp, for example, a surgeon, rotates the main body 20 of the lamp unit 8 according to the nature of surgery or an affected part and adjusts a range of light irradiated by the lamp unit 8, for example, a spot.

Thereafter, the medical headlamp captures the user's eyes by using the capturing unit 10 included in the medical headlamp.

Thereafter, information regarding an image captured by the capturing unit 10 is provided to the control unit 12 so that the medical headlamp calculates eye locations and operates the driving unit 4 installed and connected to the control unit 12 according to the calculated eye locations.

Thereafter, as the driving unit 4 operates, the location adjustment unit 6 and the lamp unit 8 which are sequentially installed and connected to the driving unit 4 move so that the lamp unit 8 can irradiate light according to user's eyes.

While this invention has been particularly shown and described with reference to preferred embodiments thereof, it will be understood by those skilled in the art that various changes in form and details may be made therein without departing from the spirit and scope of the invention as defined by the appended claims. The preferred embodiments should be considered in descriptive sense only and not for purposes of limitation. Therefore, the scope of the invention is defined not by the detailed description of the invention but by the appended claims, and all differences within the scope will be construed as being included in the present invention.

INDUSTRIAL APPLICABILITY

A headlamp according to the present invention may be applied to a field, for example, a repair business, mining industry, etc. requiring a headlamp that is put on a user and irradiates light onto a desired location according to the user's eyes, as well as the medical field.

The invention claimed is:
1. A medical headlamp comprising:
a main body put on a head;
a driving unit installed and connected to one side of the main body and to provide a driving force;
a location adjustment unit installed and connected to one side of the driving unit;
a lamp unit installed and connected to one side of the location adjustment unit, to move along with a movement of the location adjustment unit, and irradiate light onto one side of a front end thereof;
a capturing unit installed and connected to one side of the main body and to capture eye locations;
a control unit installed and connected to the driving unit and the capturing unit, to analyze an image captured by the capturing unit, calculate the eye locations by using a method of distances between the boundaries of the pupils and the eye regions, and operate the driving unit according to the calculated eye locations;

a power supply unit installed and connected to the control unit, the driving unit and the lamp unit to apply a current thereto wherein the lamp unit comprises:

a housing for providing external appearance of the lamp unit;

a body having a groove and located inside the housing; and a lamp inserted into the groove of the body and seated therein wherein the light irradiating range is changed by a variation of exposure area of the lamp in accordance with a rotation of the body.

2. The medical headlamp of claim 1, wherein the driving unit is a motor.

3. The medical headlamp of claim 1, wherein the location adjustment unit is in a plate shape.

4. The medical lamp unit of claim 1, wherein the capturing unit comprises two capturing units so that the two capturing units are adjacent to the left and right eyes.

* * * * *

UNITED STATES PATENT AND TRADEMARK OFFICE
CERTIFICATE OF CORRECTION

PATENT NO. : 8,727,558 B2  
APPLICATION NO. : 13/515766  
DATED : May 20, 2014  
INVENTOR(S) : SungMin Kim et al.

Page 1 of 1

It is certified that error appears in the above-identified patent and that said Letters Patent is hereby corrected as shown below:

Title Page, item (73), Assignee, please add YESU HOSPITAL MANAGEMENT FOUNDATION, JEOLLABUK-DO (KR).

Signed and Sealed this  
Twenty-eighth Day of October, 2014

Michelle K. Lee  
*Deputy Director of the United States Patent and Trademark Office*